United States Patent
Olsen et al.

(12) 
(10) Patent No.: US 6,613,877 B2
(45) Date of Patent: *Sep. 2, 2003

(54) HUMAN STANNIOCALCIN-ALPHA

(75) Inventors: Henrick S. Olsen, Gaithersburg, MD (US); Robert D. Fleischmann, Gaithersburg, MD (US)

(73) Assignee: Human Genome Sciences, Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/361,736

(22) Filed: Jul. 28, 1999

(65) Prior Publication Data

US 2002/0102634 A1 Aug. 1, 2002

Related U.S. Application Data

(60) Division of application No. 08/460,529, filed on Jun. 2, 1995, now Pat. No. 5,994,103, which is a continuation-in-part of application No. PCT/US94/13206, filed on Nov. 10, 1994.

(51) Int. Cl.[7] ................... C07K 14/00; C07K 14/435; C07K 14/47
(52) U.S. Cl. ................ 530/324; 530/350; 530/399
(58) Field of Search .......................... 530/350, 399, 530/324; 436/501

(56) References Cited

U.S. PATENT DOCUMENTS

| 5,447,841 A | 9/1995 | Gray et al. |
| 5,491,224 A | 2/1996 | Bittner et al. |
| 5,525,524 A | 6/1996 | Buechler et al. |
| 5,538,869 A | 7/1996 | Siciliano et al. |

FOREIGN PATENT DOCUMENTS

| WO | WO 88/03949 | 2/1988 |

OTHER PUBLICATIONS

Wagner, G.F. et al. Mol. And Cell. Endoc., 90(1): pp. 7–15 (1992).

Butkus, A. et al. Mol. And Cell. Endoc., 54: pp. 123–133 (1987).

Stern, P.H. et al. J. of Bone and Mineral Res., 6(11): pp. 1153–1159 (1991).

George et al., *Macromolecular Sequencing and Synthesis Selected Methods and Applications*, pp. 127–149 (1988).

Galzie et al. Fibroblast growth factors and their receptors. Biochem. Cell. Biol. 75: 669–685, (1997).*

* cited by examiner

*Primary Examiner*—Christine J. Saoud
(74) *Attorney, Agent, or Firm*—Human Genome Sciences, Inc.

(57) ABSTRACT

A human stanniocalcin-alpha polypeptide and DNA (RNA) encoding such polypeptide and a procedure for producing such polypeptide by recombinant techniques is disclosed. Also disclosed are methods for utilizing such polypeptide for the regulation of electrolyte imbalances which can lead to renal, bone and heart diseases and osteoporosis and Paget's Disease. Antagonists against such polypeptides and their use in the regulation of electrolyte imbalances which can lead to hypocalcemia and osteoporosis are also disclosed.

9 Claims, 4 Drawing Sheets

FIG. 1A

```
GAATTCGGCACGAGAGGAGGAGGAAGAGGGGAGCACAAAGGATCCAGTCTCCCGAC

GGGAGGTTAATACCAAGAACCATGTGCCGAGCGGCTGGGCGCTGGGCCAGTTCATGACCCTGGCT
                        MetCysAlaGluArgLeuGlyGlnPheMetThrLeuAla  13
     1

TTGGTGTGTTGGCCACCTTTGACCCGGCGCGGGGACCGACGCCACCAACCCACCCGAGGGT
LeuValLeuAlaThrPheAspProAlaArgGlyThrAspAlaThrAsnProProGluGly  33
    14

CCCCAAGACAGGAGCTCCCAGCAGAAAGGCCCGCCTGTCCCTGCAGAATACAGGGAGATC
ProGlnAspArgSerSerGlnGlnLysGlyArgLeuSerLeuGlnAsnThrAlaGluIle  53
    34

CAGCACTGTTTGGTCAACGCTGGCGATGTGGGCGTGTTTGAATGTTTCGAGAAC
GlnHisCysLeuValAsnAlaGlyAspValGlyCysGlyValPheGluCysPheGluAsn  73
    54

AACTCTTGTGAGATTCGGGGCTTACATGGATTTGCATGACTTTTCTGCACAACGCTGA
AsnSerCysGluIleArgGlyLeuHisGlyIleCysMetThrPheLeuHisAsnAlaGly  93
    74

AAATTTGATGCCCAGGGCAAGTCATTCATCAAAGACGCCTTGAAATGTAAGGCCCACGCT
LysPheAspAlaGlnGlyLysSerPheIleLysAspAlaLeuLysCysLysAlaHisAla 113
    94

CTGCGGCACAGGTTCGGCTGCATAAGCCGGAAGTGCCCGGCCATCAGGAAATGGTGTCC
LeuArgHisArgPheGlyCysIleSerArgLysCysProAlaIleArgLysGluMetValSer 133
   114
```

FIG. 1B

```
      CAGTTGCAGCGGGAATGCTACCTCAAGCACGACCTGTGCGGCTGCCCAGGAGAACACC
134   GlnLeuGlnArgGluCysTyrLeuLysHisAspLeuCysAlaAlaAlaGlnGluAsnThr   153

CGGGTGATAGTGGAGATGATCCATTTCAAGGACTTGCTGCTGCACGAACCCTACGTGGAC
154   ArgValIleValGluMetIleHisPheLysAspLeuLeuLeuHisGluProTyrValAsp   173

CTCGTGAACTTGCTGCTGACCTGTGGGGAGGTGAAGGAGGCCATCACCCACAGCGTG
174   LeuValAsnLeuLeuLeuThrCysGlyGluValLysGluAlaIleThrHisSerVal      193

CAGGTTCAGTGTGAGCAGAACTGGGGAAGCCTGTGCTCCATCTTGAGCTTCTGCACCTCG
194   GlnValGlnCysGluGlnAsnTrpGlySerLeuCysSerIleLeuSerPheCysThrSer   213

GACATCCAGAAGCCTCCCACGGCCCCCCCGAGCGCCAGGTGGACAGAACCAAG
114   AspIleGlnLysProProThrAlaProProGluArgGlnProGlnValAspArgThrLys   233

CTCTCCAGGGCCCACGGGGAAGAAGGACATCACCTCCCAGAGCCCAGGAGTAGGA
134   LeuSerArgAlaHisHisGlyGlyArgArgThrSerProProArgAlaGlnGlu         251

GACTGGCCGAGGTGCCAAGGGTGAGCGAGGTAGCAAGAGCCACCCAAACGCC
```

FIG. 2

```
    SQQKGRLSLQNTAEIQHCLVNAGDVGCGVFECFENNSCEIRGLHGICMTFLHNAGKFDAQ
    S + R S  + +++  CL A  VGC F C +N++C   G+H IC +FLH A KFD Q
 16 SPRTARFSASSPSDVARCLNGALQVGCSAFACLDNSTCNTDGMHEICRSFLHGAAKFDTQ  86

GKSFIKDALKCKAHALRHRFGCISRKCPAIREMVSQLQRECYLKHDLCAAAQENTRVIVE
    GK+F+K++LKC A+ + +      R+C +  ++M+S++Q ECY K DLC+ AQ N  + E
 87 GKTFVKESLKCIANGITSKVFLTIRRCSSFQKMISEVQEECYSKLDLCSVAQSNPEAMGE  146

MIHFKDLLLHEPYVDLVNLLLTGEEVKEAITHSVQVQCEQNWGSLCSIL
    +   + Y  L+  LLTC E+  E + + + + E  G L  +L
147 VAQVPSQFPNRYYSTLLQSLLTCDEDTVEQVRAGLVSRLEPEMGVLFQLL  196
```

```
                              10        20        30        40
                    MLQNSAVLLVLVISASATHEAEQNDSVSPRKSRVAAQNSAEVV
                    :::::: :::: |:: |::|: |::|| |: 
     MCAERLGQFMTLALVLATFDPARGTDATNPPEGPQDRSSQQKGRLSLQNTAEIQ
              10        20        30        40        50
                                                        60        70
RCLNSALQVGCGAFACLENSTCDTDGMYDICKSFLYSAAKFDTQGKAFVKESLKCIANGV
:|| :| :|||:||:|:: |:::||::||:|:||||||:|:|:||| |::: 
HCLVNAGDVGCGVFECFENNSCEIRGLHGICMTFLHNAGKFDAQGKSFIKDALKCKAHAL
  80        90       100       110       120       130
                        80        90       100       110       120       130
TSKVFLAIRRCSTFQRMIAEVQEECYSKLNVCSIAKRNPEAITEVVQLPNHFSNRYYNRL
: |:::: ::|| :| |: :|:||:|| :|||||:| 
RHRFGCISRKCPAIREMVSQLQRECYLKHDLCAAAQENTRVIVEMIHFKDLLHEPYVDL
  140       150       160       170       180       190
                        140       150       160
VRSLLECDEDTVSTIRDSLMEKIGPNMASLFHILQ-TDHCAQTHPRADFNRRTNEPQKL
|: ||:||: :: ::|| :|| || : :|:: :: ||:||
VNLLLTCGEEVKEAITHSVQVCEQNWGSLCSILSFCTSDIQKPPTAPPERQPVDRTKL
  200       210       220       230       240       250

KVLLRNLRGEEDSPSHIKRTSHESA
  230       240

SRAHHGGRRTSPPRAQE

FIG. 3
```

HUMAN STANNIOCALCIN-ALPHA

This application is a Divisional of U.S. application No. 08/460,529 filed Jun. 2, 1995 and issued as U.S. Pat. No. 5,994,103 on Nov. 30, 1999, which is a Continuation-In-Part of PCT/U594/13206 filed Nov. 10, 1994.

This invention relates to newly identified polynucleotides, polypeptides encoded by such polynucleotides, the use of such polynucleotides and polypeptides, as well as the production of such polynucleotides and polypeptides. More particularly, the polypeptide of the present invention has putatively been identified as human stanniocalcin-alpha. The invention also relates to inhibiting the action of such polypeptides.

Stanniocalcin (formerly known as both teleocalcin and hypocalcin) is an anti-hypercalcemic, glycoprotein hormone that is produced by the corpuscles of stannius, endocrine glands of the bony fishes. Humans also produce a stanniocalcin glycoprotein.

Stanniocalcin-alpha has similar reported biological activities to parathyroid hormone (PTH) and both of these proteins exhibit dual functions in mammals. They exert hypercalcemic activity possibly due to stimulation of bone resorption (Endocrinology 119:2249–2255 (1986)) and hypocalcaemic activity in fish. The hypocalcaemic activity is possibly due to inhibition of gill calcium influx (J. Exp. Biol., 140:199–208 (1988)). Further, PTH has a biphasic action on bone metabolism, i.e., at low doses it increases bone formation, while at high doses it increases bone resorption. Accordingly, both the polypeptide itself and an antagonist, under different circumstances, may be used to treat osteoporosis.

The Corpuscles of Stannius protein of non-humans has been studied extensively. Recently, a Corpuscles of Stannius protein has been purified and cloned from *Anquilla australis*. The kidneys of teleost fish have been found to contain secretory granules, the Corpuscles of Stannius. Electron microscopy indicates that the granules are of a proteinaceous nature and may represent hormones or enzymes of unrecognized physiological and biochemical function (Butkus, A. et al. Mol. Cell Endocrinol, 54:123–33 (1987)).

There has also been isolated and purified a glycoprotein from the Corpuscles of Stannius of trout, which is considered hypocalcin, the major hypocalcemic hormone of fish. This product is present in relatively large amounts in the Corpuscles of Stannius of several species (i.e., European eel, tilapia goldfish, and carp). Hypocalcin is typically released from the Corpuscles of Stannius in response to an experimentally induced increase of the blood calcium concentration. Ultrastructural observations show that after this treatment the hypocalcin-producing cell type of the corpuscles of stannius are almost completely degranulated. The isolated glycoprotein has an apparent molecular weight of 54 kDa. (Lafeber F. P. et al., Gen Comp. Endocrinol, 69:19–30 (1988)).

Moreover, it has recently been shown that several synthetic peptide fragments of teleocalcin inhibit calcium uptake in juvenile rainbow trout (Salmo Gairdneri). The N-terminal peptides (amino acids 1 to 20) of both eel and salmon teleocalcin significantly inhibit $^{45}$Ca uptake at the high point of the calcium uptake cycle (up to 75%), although the effective doses of the peptides on a molar basis were 20 to 200 times that of the intact molecule. In contrast, the C-terminal fragment of eel teleocalcin (amino acids 202 to 231) did not have an inhibitory effect on calcium uptake (Milliken C. E. et al., Gen. Comp. Endocrinol, 77:416–22 (1990)).

There has also been a description of the purification and characterization of two salmon stanniocalcins, and the examination of the regulation of hormone secretion in response to calcium using both in vitro and in vivo model systems. The molecular cloning and cDNA sequence analysis of a coho salmon stanniocalcin messenger RNA (mRNA) from a salmon CS lambda gt10 cDNA library is described. The stanniocalcin mRNA in salmon is approximately 2 kDa in length and encodes a primary translation product of 256 amino acids. The first 33 residues comprise the preprotein region of the hormone, whereas the remaining 223 residues make up the mature form of the hormone. (Wagner G. F. et al., Mol. Cell Endocrinol, 90:7–15 (1992)).

The polypeptide of the present invention has been putatively identified as human stanniocalcin-alpha. This identification has been made as a result of amino acid sequence homology.

In accordance with one aspect of the present invention, there is provided a novel putative mature polypeptide which is human stanniocalcin-alpha, as well as biologically active and diagnostically or therapeutically useful fragments, analogs and derivatives thereof.

In accordance with another aspect of the present invention, there are provided isolated nucleic acid molecules encoding human stanniocalcin-alpha, including mRNAs, DNAs, cDNAs, genomic DNA as well as antisense analogs thereof and biologically active and diagnostically or therapeutically useful fragments thereof.

In accordance with yet a further aspect of the present invention, there is provided a process for producing such polypeptide by recombinant techniques comprising culturing recombinant prokaryotic and/or eukaryotic host cells, containing a human stanniocalcin-alpha nucleic acid sequence, under conditions promoting expression of said protein and subsequent recovery of said protein.

In accordance with yet a further aspect of the present invention, there is provided a process for utilizing such polypeptide, or polynucleotide encoding such polypeptide, for therapeutic purposes, for example, to treat electrolyte disorders which lead to renal, and heart diseases and, due to a biphasic action of the polypeptide it may be employed to treat, osteoporosis, Paget's Disease and osteopetrosis.

In accordance with yet a further aspect of the present invention, there are provided antibodies against such polypeptides.

In accordance with yet another aspect of the present invention, there are provided antagonists to such polypeptides, which may be used to inhibit the action of such polypeptides, for example, in the treatment of osteoporosis and hypocalcemia. Hypocalcemia can arise from a number of different causes including renal failure, hyperparathyroidism, severe infections, pancreatic insufficiency or burns which trap calcium from the intercellular fluid. Hypocalcemia results in tetany, convulsions and other related disorders.

In accordance with still another aspect of the present invention, there are provided nucleic acid probes comprising nucleic acid molecules of sufficient length to specifically hybridize to human stanniocalcin-alpha sequences.

These and other aspects of the present invention should be apparent to those skilled in the art from the teachings herein.

BRIEF DESCRIPTION OF THE DRAWING

The following drawings are illustrative of embodiments of the invention and are not meant to limit the scope of the invention as encompassed by the claims.

FIG. 1 displays the cDNA sequence and corresponding deduced amino acid sequence of the human stanniocalcin-alpha protein (SEQ ID NO:2). The standard three-letter abbreviations for amino acids are used.

FIG. 2 is an amino comparison of stanniocalcin from *Anguilla Australis* (SEQ ID NO:9, lower line) and human stanniocalcin-alpha (SEQ ID NO:2, upper line). There are 35% identical amino acid residues in a 170 amino acid overlap and a total similarity of 55%.

FIG. 3 is an amino acid sequence comparison of human stanniocalcin (SEQ ID NO:10, upper line) and human stanniocalcin-alpha (SEQ ID NO:2, lower line).

In accordance with an aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the cDNA of the clone deposited as ATCC Deposit No. 75831 on Jul. 15, 1994 (SEQ ID NO:12).

The ATCC number referred to above is directed to a biological deposit with the ATCC, 10801 University Boulevard, Manassas, Va. 20110-2209. Since the strain referred to is being maintained under the terms of the Budapest Treaty, it will be made available to a patent office signatory to the Budapest Treaty.

The polynucleotide of this invention was discovered in a cDNA library derived from lung fibroblast cells. It is structurally related to the human stanniocalcin family. It contains an open reading frame encoding a protein of about 251 amino acid residues of which approximately the first 40 amino acid residues are the putative leader sequence such that the mature protein comprises 211 amino acids. The protein exhibits the highest degree of homology to human stanniocalcin with 28% identity and 64% similarity over the entire amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA (SEQ ID NO:11).

The polynucleotide which encodes for the mature polypeptide of FIG. 1 or for the mature polypeptide encoded by the deposited cDNA (SEQ ID NO: 12) may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 or the polypeptide encoded by the cDNA of the deposited clone (SEQ ID NO:12). The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 or the same mature polypeptide encoded by the cDNA of the deposited clone (SEQ ID NO:12) as well as variants of such polynucleotides which variants encode for a fragment, derivative or analog of the polypeptide of FIG. 1 or the polypeptide encoded by the cDNA of the deposited clone (SEQ ID NO:12). Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–B or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence is preferably a hexahistidine tag supplied by a vector, for example a pQE-9 or pQE-60 vector, to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length polynucleotide of the invention may be used as a hybridization probe for a cDNA library to isolate the full length cDNA and to isolate other cDNA which have a high sequence similarity to the full length polynucleotide of the invention. Probes of this type preferably have at least 10, 20 or 30 bases and may contain, for example, 50 or more bases. The probe may also be used to identify a cDNA clone corresponding to a full length transcript and a genomic clone or clones that contain the complete gene of the invention including regulatory and promotor regions, exons, and introns. An example of a screen comprises isolating the coding region of the full length gene of the invention by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIG. 1 or the deposited cDNA (SEQ ID NO:11).

Alternatively, the polynucleotide may have at least 20 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a human stanniocalcin-alpha polypeptide which has the deduced amino acid sequence of FIG. 1 or which has the amino acid sequence encoded by the deposited cDNA (SEQ ID NO:12), as well as fragments, analogs and derivatives of such polypeptide.

The terms "fragment," "derivative" and "analog" when referring to the polypeptide of FIG. 1 or that encoded by the deposited cDNA (SEQ ID NO:12), means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the mature polypeptide of FIG. 1 (SEQ ID NO:2) or that encoded by the deposited cDNA (SEQ ID NO:12) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues include a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.$ $coli,$ Streptomyces, *Salmonella typhimurium;* fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, PXT1, pSG (Stratagene) pSVK3, PBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation, systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10% 300 bp that act on a promoter to increase its transcription. Examples include the SV40 enhancer on the late side of the replication origin bp 100% to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of $E.$ $coli$ and $S.$ $cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

Human stanniocalcin-alpha administration may be used for therapeutic treatment of numerous electrolyte-based diseases. One cause of arterial hypertension is abnormal $Na^+$ transport across the cell wall of the vascular smooth muscle cells due to a defect in or inhibition of the $Na^+$-$K+$ pump, another is increased permeability to $Na^+$ as has been described in some forms of human hypertension. The net result is an increase in intra-cellular $Na^+$, which makes the cell more sensitive to vasoconstrictive agents. Since $Ca^{++}$ follows $Na^+$, it is postulated that it is the accumulation of intra-cellular $Ca^{++}$ and not $Na^+$ per se that is responsible for increased sensitivity to sympathetic stimulation. Accordingly, since human stanniocalcin-alpha can function as a hypocalcemic agent, it can help to offset this increased intra-cellular $Ca^{++}$ and reduce or prevent hypertension.

Further, hypercalcemia has been implicated in heart dysrythmias, coma, and cardiac arrest. Accordingly, human stanniocalcin-alpha may have therapeutic value for the treatment of these disorders by lowering the concentration of free $Ca^{2+}$.

Hypertension is also directly related to renal disorders. Accordingly, a higher or lower than normal concentration of electrolytes can cause renal malfunction and directly lead to other disorders. As an example, $Ca^{++}$-phosphorous imbalance can cause muscle and bone pain, demineralization of the bones and calcification in various organs including the brain, eyes, myocardia and blood vessels. Accordingly, the polypeptide of the present invention may be used to offset disorders that are due to a $Ca^{++}$-phosphate imbalance. Renal failure itself leads to an abnormally high concentration of phosphate in the blood which can be reduced to normal concentrations by human stanniocalcin-alpha.

Human stanniocalcin-alpha is also useful for the treatment of certain bone diseases, in that, it may have a biphasic action on bone metabolism, i.e., at low doses it may increase bone formation, while at high doses it increases bone resorption. Therefore, administration of low doses of human stanniocalcin-alpha may be employed to treat osteoporosis and administration of high doses may be employed to treat osteopetrosis, which is an overgrowth and sclerosis of bone with the marked thickening of the bony cortex and narrowing or filling of the marrow cavity.

The causes of hypercalcemia may also be a number of different disorders including hyperparathyroidism, hypervitaminosis D, tumors that raise the serum $Ca^{++}$ levels by destroying bone, sarcoidosis, hyperthyroidism, adrenal insufficiency, loss of serum albumin, secondary renal diseases, excessive gastrointestinal calcium absorption and elevated concentration of plasma proteins. Accordingly, human stanniocalcin-alpha is effective in reducing hypercalcemia and its related disorders.

Human stanniocalcin-alpha may also be employed for the treatment of other disorders relating to unusual electrolyte concentrations and fluid imbalance, for example, migraine headaches.

This invention provides a method for identification of human stanniocalcin-alpha receptors. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to human stanniocalcin-alpha, and a cDNA library created from this RNA is divided into pools and used to transfect COS cells or other cells that are not responsive to the human stanniocalcin-alpha protein. Transfected cells which are grown on glass slides are exposed to labeled human stanniocalcin-alpha. The stanniocalcin-alpha can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone that encodes the putative receptor.

As an alternative approach for receptor identification, labeled human stanniocalcin-alpha can be photoaffinity linked with cell membrane or extract preparations that express the receptor molecule. Cross-linked material is resolved by PAGE and exposed to X-ray film. The labeled complex containing the ligand-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

This invention also provides a method of screening compounds to identify agonists and antagonists of human stanniocalcin-alpha. As an example, a bioassay may be performed wherein the assay components comprise a mammalian cell or membrane preparation expressing a human stanniocalcin-alpha receptor on the surface thereof, labeled calcium, for example $^{45}Ca^{++}$, and the compound to be screened. If the compound is an effective human stanniocalcin-alpha agonist it will mimic the human stanniocalcin-alpha receptor ligand such that there is $^{45}Ca^{++}$ uptake by the cell or membrane in the absence of human stanniocalcin-alpha. The amount of $^{45}Ca^{++}$ uptake can be determined by taking advantage of the radioactive label. When screening for an antagonist, human stanniocalcin-alpha is added to the bioassay and the ability of the compound to inhibit $^{45}Ca^{++}$ uptake by interfering with the interaction of human stanniocalcin-alpha and its receptor can be determined in the same manner.

Alternatively, the response of a known second messenger system following interaction of human stanniocalcin-alpha and the receptor would be measured and compared in the presence and absence of the compound. Such second messenger systems include but are not limited to, cAMP guanylate cyclase, ion channels or phosphoinositide hydrolysis.

Potential human stanniocalcin-alpha antagonists include antibodies or in some cases, oligonucleotides, which bind to huam stanniocalcin-alpha and eliminate its function. Antagonists also include polypeptides which bind to human stanniocalcin-alpha receptors and effectively block the receptor from human stanniocalcin-alpha. These polypeptides are proteins which are closely related to human stanniocalcin-alpha -but have lost natural biological function, an example is a mutated form of human stanniocalcin-alpha.

Human stanniocalcin-alpha antagonists also include antisense constructs. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10% to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251:1360 (1991)), thereby preventing transcription and the production of human stanniocalcin-alpha. The antisense RNA oligonucleotide hybridizes to the mRNA in vivo and blocks translation of the mRNA molecule into the human stanniocalcin-alpha polypeptide (Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of human stanniocalcin-alpha protein.

Human stanniocalcin-alpha antagonists also include small molecules which bind to the active site of the polypeptide making it unable to impart biological function. Examples of small molecules include but are not limited to small peptides or peptide-like molecules.

The antagonists may be employed to block the stimulation of bone resorption by a high concentration of human stanniocalcin-alpha and, accordingly, may be employed to treat osteoporosis.

The human stanniocalcin-alpha antagonists may also be employed to treat hypocalcemia and Paget's disease among other disorders where an increase in calcium levels is desired. The antagonists may be employed in a composition with a pharmaceutically acceptable carrier, e.g., as hereinafter described.

The human stanniocalcin-alpha polypeptides of the present invention, and agonist and antagonist compounds, may be employed in combination with a suitable pharmaceutical carrier. Such pharmaceutical compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc.

The human stanniocalcin-alpha polypeptides, and agonists and antagonists which are also polypeptides, may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques,* Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified-retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy,* Vol. 1, pgs. 5-14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the stanniocalcin-alpha gene as part of a diagnostic assay for detecting diseases or susceptibility to diseases related to the presence of mutated human stanniocalcin-alpha. Such diseases are related to an under-expression of human stanniocalcin-alpha, for example, hypertension.

Individuals carrying mutations in the human stanniocalcin-alpha gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding human stanniocalcin-alpha can be used to identify and analyze human stanniocalcin-alpha mutations. For example, deletions and insertions can be detected by a change in size of the amplified product in comparison to the normal genotype. Point mutations can be identified by hybridizing amplified DNA to radiolabeled human stanniocalcin-alpha RNA or alternatively, radiolabeled human stanniocalcin-alpha antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamidine gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the sequence is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5% to 50 µg of DNA are digested with 20% to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of Human Stanniocalcin-Alpha

The DNA sequence encoding human stanniocalcin-alpha ATCC #75831 (SEQ ID NO:11), is initially amplified using PCR oligonucleotide primers corresponding to the 5' and 3' sequences of the stanniocalcin-alpha coding sequences. The 5' oligonucleotide primer has the sequence 5' GACTACAT-GTGTGCCGAGCGGCTGGG 3' (SEQ ID NO:3) contains a Afl III restriction enzyme site and 20 nucleotides of stanniocalcin-alpha coding sequence starting from the presumed methionine start codon. The 3' sequence 5' GACTA-GATCTCTCCTGGGCTCTGGGAGGTG 3' (SEQ ID NO:4) contains complementary sequences to a Bgl II site and is followed by 20 nucleotides of stanniocalcin-alpha. A pQE-60 vector (Qiagen, Inc. 9259 Eton Avenue, Chatsworth, Calif., 91311) encodes antibiotic resistance (Amp$^r$), a bacterial origin of replication (ori), an IPTG-regulatable promoter operator (P/O), a ribosome binding site (RBS), a 6-His tag and restriction enzyme sites. pQE-60 is digested with Afl III and Bgl II. The amplified sequences are ligated into pQE-60 after digestion with Afl III and Bgl II and are inserted in frame with the sequence encoding for the histidine tag and the RBS. The ligation mixture is then used to transform the E. coli strain M15/rep 4 available from Qiagen by the procedure described in Sambrook, J. et al., Molecular Cloning: A Laboratory Manual, Cold Spring Laboratory Press, (1989). M15/rep4 contains multiple copies of the plasmid pREP4, which expresses the lad repressor and also confers kanamycin resistance (Kan$^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation (20 mins at 6000Xg). The cell pellet is solubilized in the chaotropic agent 6 Molar Guanidine HCl. After clarification, solubilized stanniocalcin-alpha is purified from this solution by chromatography on a Nickel-Chelate column under conditions that allow for tight binding by proteins containing the 6-His tag (Hochuli, E. et al., Genetic Engineering, Principles & Methods, 12:87–98 (1990)). Protein renaturation out of GnHCl can be accomplished by several protocols (Jaenicke, R. and Rudolph, R., Protein Structure—A Practical Approach, IRL Press, New York (1990)). Initially, step dialysis is utilized to remove the GnHCL. Alternatively, the purified protein isolated from the Ni-chelate column can be bound to a second column over which a decreasing linear GnHCL gradient is run. The protein is allowed to renature while bound to the column and is subsequently eluted with a buffer containing 250 mM Imidazole, 150 mM NaCl, 25 mM Tris-HCl pH 7.5 and 10% Glycerol. Finally, soluble protein is dialyzed against a storage buffer containg 5 mM Ammonium Bicarbonate. The purified protein was analyzed by SDS-PAGE (FIG. 4).

EXAMPLE 2

Expression of Recombinant Human Stanniocalcin-Alpha in COS Cells

The expression of plasmid, stanniocalcin-alpha HA is derived from a vector pcDNAI/Amp (Invitrogen) containing: 1) SV40 origin of replication, 2) ampicillin resistance gene, 3) E. coli replication origin, 4) CMV promoter followed by a polylinker region, an SV40 intron and polyadenylation site. A DNA fragment encoding the entire stanniocalcin-alpha precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows:

The DNA sequence encoding stanniocalcin-alpha was constructed by PCR on the original express sequence tag (EST) cloned using two primers: the 5' primer 5'GAC-TAAGCTTA TGTGTGCCGAGCGGCTGGGC 3' (SEQ ID NO:5) contains a Hind III site followed by 21 nucleotides of stanniocalcin-alpha coding sequence starting from the initiation codon; the 3' sequence 5' GACTTCTAGAC-TAAGCGTAGTCTGGGACGTCGTATGGG-TACTCCTGGGCTCTGGG AGGTG 3' (SEQ ID NO:6) contains complementary sequences to an Xba I site, translation stop codon, HA tag and the last 20 nucleotides of the stanniocalcin-alpha coding sequence (not including the stop codon). Therefore, the PCR product contains a Hind III site, stanniocalcin-alpha coding sequence followed by HA tag fused in frame, a translation termination stop codon next to the HA tag, and an Xba I site. The PCR amplified DNA fragment and the vector, pcDNAI/Amp, were digested with Hind III and Xba I restriction enzyme and ligated. The ligation mixture was transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant stanniocalcin-alpha, COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the stanniocalcin-alpha HA protein was detected by the radiolabelling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media was then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media were precipitated with an HA specific monoclonal antibody. Proteins precipitated were analyzed on 15% SDS-PAGE gels.

EXAMPLE 3

Cloning and Expression of Human Stanniocalcin-Alpha using the Baculovirus Expression System The DNA sequence encoding the full length stanniocalcin-alpha protein, ATCC #75831 (SEQ ID NO:11), is amplified using PCR oligonucleotide primers corresponding to the 5' and 3' sequences of the gene.

The 5' primer has the sequence 5' GACTGGATCCGC-CACCATGTGTGCCGAGCGGCTGGGC 3' (SEQ ID NO:7) and contains a BamHI restriction enzyme site (in bold) followed by 6 nucleotides resembling an efficient signal for the initiation of translation in eukaryotic cells (Kozak, M., J. Mol. Biol., 196:947–950 (1987) which is just behind the first 21 nucleotides of the stanniocalcin-alpha gene (the initiation codon for translation "ATG" is underlined).

The 3' primer has the sequence 5' GACTGGTAC-CCTACTCCTGGGCTCTGGGAGG 3' (SEQ ID NO:8) and contains the cleavage site for the restriction endonuclease Asp 718 and 21 nucleotides complementary to the 3' sequence of the stanniocalcin-alpha gene. The amplified sequences are isolated from a 1% agarose gel using a commercially available kit ("Geneclean," BIO 101 Inc., La Jolla, Calif.). The fragment is then digested with the endonucleases BamHI and Asp 718 and then purified again on a 1% agarose gel. This fragment is designated F2.

The vector pRG1 (modification of pVL941 vector, discussed below) is used for the expression of the stanniocalcin-alpha protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the *Autographa californica* nuclear polyhedrosis virus (AcMNPV) followed by the recognition sites for the restriction endonucleases BamHI and Asp 718. The polyadenylation site of the simian virus (SV)40 is used for efficient polyadenylation. For an easy selection of recombinant viruses the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid is digested with the restriction enzymes BamHI and Asp 718 and then dephosphorylated using calf intestinal phosphatase by procedures known in the art. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. *E. coli* HB101 cells are then transformed and bacteria identified that contained the plasmid (pBac-stanniocalcin-alpha) with the stanniocalcin-alpha gene using the enzymes BamHI and Asp 718. The sequence of the cloned fragment is confirmed by DNA sequencing.

5 µg of the plasmid pBac-stanniocalcin-alpha is cotransfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 µg of BaculoGold™ virus DNA and 5 µg of the plasmid pBac-stanniocalcin-alpha are mixed in a sterile well of a microtiter plate containing 50 µl of serum free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added dropwise to the Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses are added to the cells, blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculoviruses is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-stanniocalcin-alpha at a multiplicity of infection (MOI) of 2. Six hours later the medium is removed and replaced with SF900 II medium minus methionine and cysteine (Life Technologies Inc., Gaithersburg). 42 hours later 5 pCi of $^{35}$S-methionine and 5 µCi $^{35}$S cysteine (Amersham) are added. The cells are further incubated for 16 hours before they are harvested by centrifugation and the labelled proteins visualized by SDS-PAGE and autoradiography (FIG. 5). In FIG. 5 the gel indicates that stanniocalcin-alpha exists as a homodimer.

EXAMPLE 4

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 100% FBS, penicillin and streptomycin, is added. This is then incubated at 37° C for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219-25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer $further includes a HindIII site. Equal quantities of the Moloney murine sarcoma virus linear backbone and the amplified $EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polypeptide comprising an amino acid sequence selected from the group consisting of:
   (a) at least 30 contiguous amino acid residues of a human stanniocalcin-alpha polypeptide encoded by the human cDNA clone contained in ATCC Deposit No. 75831;
   (b) the amino acid sequence of the full-length human stanniocalcin-alpha polypeptide encoded by the human cDNA clone contained in ATCC Deposit No. 75831;
   (c) the amino acid sequence of the full-length length human stanniocalcin-alpha polypeptide, encoded by the human cDNA clone contained in ATCC Deposit No. 75831, excluding the N-terminal methionine residue.

2. The isolated polypeptide of claim 1, wherein said amino acid sequence is (a).

3. The isolated polypeptide of claim 2, wherein said amino acid sequence comprises at least 50 amino acid residues of the amino acid sequence encoded by the human cDNA clone contained in ATCC Deposit No. 75831.

4. The isolated polypeptide of claim 3, wherein said amino acid sequence is further fused to a heterologous polypeptide.

5. The isolated polypeptide of claim 2, wherein said amino acid sequence comprises the amino acid sequence of the full-length human stanniocalcin-alpha polypeptide encoded by the cDNA clone contained in ATCC Deposit No. 75831, excluding the N-terminal methionine residue.

6. The isolated polypeptide of claim 5, wherein said amino acid sequence comprises the amino acid sequence of the full-length human stanniocalcin-alpha polypeptide encoded by the human cDNA clone contained in ATCC Deposit No. 75831.

7. The isolated polypeptide of claim 6, wherein said amino acid sequence is further fused to a heterologous polypeptide.

8. The isolated polypeptide of claim 5, wherein said amino acid sequence is further fused to a heterologous polypeptide.

9. The isolated polypeptide of claim 2, wherein said amino acid sequence is further fused to a heterologous polypeptide.

* * * * *

SEQUENCE LISTING

```
<160> NUMBER OF SEQ ID NOS: 12

<210> SEQ ID NO 1
<211> LENGTH: 892
<212> TYPE: DNA
<213> ORGANISM: human

<400> SEQUENCE: 1
gaattcggca cgagaggagg aggaggaaga ggggagcaca aaggatccag gtctcccgac      60
gggaggttaa taccaagaac catgtgtgcc gagcggctgg gccagttcat gaccctggct     120
ttggtgttgg ccacctttga cccggcgcgg gggaccgacg ccaccaaccc acccgagggt     180
ccccaagaca ggagctccca gcagaaaggc cgcctgtccc tgcagaatac agcggagatc     240
cagcactgtt tggtcaacgc tggcgatgtg gggtgtggcg tgtttgaatg tttcgagaac     300
aactcttgtg agattcgggg cttacatggg atttgcatga cttttctgca caacgctgga     360
aaatttgatg cccagggcaa gtcattcatc aaagacgcct tgaaatgtaa ggcccacgct     420
ctgcggcaca ggttcggctg cataagccgg aagtgcccgg ccatcaggga aatggtgtcc     480
cagttggagc gggaatgcta cctcaagcac gacctgtgcg cggctgccca ggagaacacc     540
cgggtgatag tggagatgat ccatttcaag gacttgctgc tgcacgaacc ctacgtggac     600
ctcgtgaact tgctgctgac ctgtggggag gaggtgaagg aggccatcac ccacagcgtg     660
```

-continued

```
caggttcagt gtgagcagaa ctgggaaagc ctgtgctcca tcttgagctt ctgcacctcg      720
gacatccaga agcctcccac ggcgccccc gagcgccagc cccaggtgga cagaaccaag       780
ctctccaggg cccaccacgg gggaagaagg acatcacctc ccagagccca ggagtaggga      840
gactggccga ggtgccaagg gtgagcgagg tagcaagagc cacccaaacg cc              892
```

<210> SEQ ID NO 2
<211> LENGTH: 251
<212> TYPE: PRT
<213> ORGANISM: human

<400> SEQUENCE: 2

```
Met Cys Ala Glu Arg Leu Gly Gln Phe Met Thr Leu Ala Leu Val Leu
 1               5                  10                  15

Ala Thr Phe Asp Pro Ala Arg Gly Thr Asp Ala Thr Asn Pro Pro Glu
                20                  25                  30

Gly Pro Gln Asp Arg Ser Ser Gln Lys Gly Arg Leu Ser Leu Gln
             35                  40                  45

Asn Thr Ala Glu Ile Gln His Cys Leu Val Asn Ala Gly Asp Val Gly
 50                  55                  60

Cys Gly Val Phe Glu Cys Phe Glu Asn Asn Ser Cys Glu Ile Arg Gly
 65                  70                  75                  80

Leu His Gly Ile Cys Met Thr Phe Leu His Asn Ala Gly Lys Phe Asp
                 85                  90                  95

Ala Gln Gly Lys Ser Phe Ile Lys Asp Ala Leu Lys Cys Lys Ala His
                100                 105                 110

Ala Leu Arg His Arg Phe Gly Cys Ile Ser Arg Lys Cys Pro Ala Ile
            115                 120                 125

Arg Glu Met Val Ser Gln Leu Gln Arg Glu Cys Tyr Leu Lys His Asp
        130                 135                 140

Leu Cys Ala Ala Ala Gln Glu Asn Thr Arg Val Ile Val Glu Met Ile
145                 150                 155                 160

His Phe Lys Asp Leu Leu Leu His Glu Pro Tyr Val Asp Leu Val Asn
                165                 170                 175

Leu Leu Leu Thr Cys Gly Glu Glu Val Lys Glu Ala Ile Thr His Ser
            180                 185                 190

Val Gln Val Gln Cys Glu Gln Asn Trp Gly Ser Leu Cys Ser Ile Leu
        195                 200                 205

Ser Phe Cys Thr Ser Asp Ile Gln Lys Pro Pro Thr Ala Pro Pro Glu
    210                 215                 220

Arg Gln Pro Gln Val Asp Arg Thr Lys Leu Ser Arg Ala His His Gly
225                 230                 235                 240

Gly Arg Arg Thr Ser Pro Pro Arg Ala Gln Glu
                245                 250
```

<210> SEQ ID NO 3
<211> LENGTH: 26
<212> TYPE: DNA
<213> ORGANISM: human

<400> SEQUENCE: 3

```
gactacatgt gtgccgagcg gctggg                                            26
```

<210> SEQ ID NO 4
<211> LENGTH: 30
<212> TYPE: DNA
<213> ORGANISM: human

<400> SEQUENCE: 4
gactagatct ctcctgggct ctgggaggtg                                    30

<210> SEQ ID NO 5
<211> LENGTH: 31
<212> TYPE: DNA
<213> ORGANISM: human

<400> SEQUENCE: 5
gactaagctt atgtgtgccg agcggctggg c                                  31

<210> SEQ ID NO 6
<211> LENGTH: 59
<212> TYPE: DNA
<213> ORGANISM: human

<400> SEQUENCE: 6
gacttctaga ctaagcgtag tctgggacgt cgtatgggta ctcctgggct ctgggaggt    59

<210> SEQ ID NO 7
<211> LENGTH: 38
<212> TYPE: DNA
<213> ORGANISM: human

<400> SEQUENCE: 7
gactggatcc gccaccatgt gtgccgagcc ggctgggc                           38

<210> SEQ ID NO 8
<211> LENGTH: 31
<212> TYPE: DNA
<213> ORGANISM: human

<400> SEQUENCE: 8
gactggtacc ctactcctgg gctctgggag g                                  31

<210> SEQ ID NO 9
<211> LENGTH: 170
<212> TYPE: PRT
<213> ORGANISM: Anguilla australis

<400> SEQUENCE: 9

Ser Pro Arg Thr Ala Arg Phe Ser Ala Ser Pro Ser Asp Val Ala
 1               5                  10                  15

Arg Cys Leu Asn Gly Ala Leu Gln Val Gly Cys Ser Ala Phe Ala Cys
                20                  25                  30

Leu Asp Asn Ser Thr Cys Asn Thr Asp Gly Met His Glu Ile Cys Arg
            35                  40                  45

Ser Phe Leu His Gly Ala Ala Lys Phe Asp Thr Gln Gly Lys Thr Phe
        50                  55                  60

Val Lys Glu Ser Leu Lys Cys Ile Ala Asn Gly Ile Thr Ser Lys Val
65                  70                  75                  80

Phe Leu Thr Ile Arg Arg Cys Ser Ser Phe Gln Lys Met Ile Ser Glu
                85                  90                  95

Val Gln Glu Glu Cys Tyr Ser Lys Leu Asp Leu Cys Ser Val Ala Gln
            100                 105                 110

Ser Asn Pro Glu Ala Met Gly Glu Val Ala Gln Val Pro Ser Gln Phe
        115                 120                 125

Pro Asn Arg Tyr Tyr Ser Thr Leu Leu Gln Ser Leu Leu Thr Cys Asp
    130                 135                 140

Glu Asp Thr Val Glu Gln Val Arg Ala Gly Leu Val Ser Arg Leu Glu
145                 150                 155                 160

Pro Glu Met Gly Val Leu Phe Gln Leu Leu
                165                 170

<210> SEQ ID NO 10
<211> LENGTH: 247
<212> TYPE: PRT
<213> ORGANISM: human

<400> SEQUENCE: 10

Met Leu Gln Asn Ser Ala Val Leu Leu Val Leu Val Ile Ser Ala Ser
1               5                   10                  15

Ala Thr His Glu Ala Glu Gln Asn Asp Ser Val Ser Pro Arg Lys Ser
                20                  25                  30

Arg Val Ala Ala Gln Asn Ser Ala Glu Val Val Arg Cys Leu Asn Ser
            35                  40                  45

Ala Leu Gln Val Gly Cys Gly Ala Phe Ala Cys Leu Glu Asn Ser Thr
        50                  55                  60

Cys Asp Thr Asp Gly Met Tyr Asp Ile Cys Lys Ser Phe Leu Tyr Ser
65                  70                  75                  80

Ala Ala Lys Phe Asp Thr Gln Gly Lys Ala Phe Val Lys Glu Ser Leu
                85                  90                  95

Lys Cys Ile Ala Asn Gly Val Thr Ser Lys Val Phe Leu Ala Ile Arg
            100                 105                 110

Arg Cys Ser Thr Phe Gln Arg Met Ile Ala Glu Val Gln Glu Glu Cys
        115                 120                 125

Tyr Ser Lys Leu Asn Val Cys Ser Ile Ala Lys Arg Asn Pro Glu Ala
130                 135                 140

Ile Thr Glu Val Val Gln Leu Pro Asn His Phe Ser Asn Arg Tyr Tyr
145                 150                 155                 160

Asn Arg Leu Val Arg Ser Leu Leu Glu Cys Asp Glu Asp Thr Val Ser
                165                 170                 175

Thr Ile Arg Asp Ser Leu Met Glu Lys Ile Gly Pro Asn Met Ala Ser
            180                 185                 190

Leu Phe His Ile Leu Gln Thr Asp His Cys Ala Gln Thr His Pro Arg
        195                 200                 205

Ala Asp Phe Asn Arg Arg Arg Thr Asn Glu Pro Gln Lys Leu Lys Val
210                 215                 220

Leu Leu Arg Asn Leu Arg Gly Glu Glu Asp Ser Pro Ser His Ile Lys
225                 230                 235                 240

Arg Thr Ser His Glu Ser Ala
                245

<210> SEQ ID NO 11
<211> LENGTH: 1024
<212> TYPE: DNA
<213> ORGANISM: human

<400> SEQUENCE: 11
ggcacgagag gaggaggagg aagaggggag cacaaaggat ccaggtctcc cgacgggagg      60
ttaataccaa gaaccatgtg tgccgagcgg ctgggccagt tcatgaccct ggctttggtg     120
ttggccacct tgacccggc gcgggggacc gacgccacca acccacccga ggtccccaa      180 gacaggagct cccagcagaa aggccgcctg tccctgcaga atacagcgga gatccagcac     240

-continued

```
tgtttggtca acgctggcga tgtgggtgt ggcgtgtttg aatgtttcga gaacaactct      300
tgtgagattc ggggcttaca tgggatttgc atgacttttc tgcacaacgc tggaaaattt    360
gatgcccagg gcaagtcatt catcaaagac gccttgaaat gtaaggccca cgctctgcgg    420
cacaggttcg gctgcataag ccggaagtgc ccggccatca gggaaatggt gtcccagttg    480
cagcgggaat gctacctcaa gcacgacctg tgcgcggctg cccaggagaa cacccgggtg    540
atagtggaga tgatccattt caaggacttg ctgctgcacg aaccctacgt ggacctcgtg    600
aacttgctgc tgacctgtgg ggaggaggtg aaggaggcca tcacccacag cgtgcaggtt    660
cagtgtgagc agaactgggg aagcctgtgc tccatcttga gcttctgcac ctcggccatc    720
cagaagcctc ccacggcgcc ccccgagcgc cagccccagg tggacagaac caagctctcc    780
agggcccacc acggggaagc aggacatcac ctcccagagc cagcagtag ggagactggc     840
cgaggtgcca aggtgagcg aggtagcaag agccacccaa acgccatgc ccgaggcaga      900
gtcgggggcc ttgggctca gggaccttcc ggaagcagcg agtgggaaga cgaacagtct    960
gagtattctg atatccggag gtgaaatgaa aggcctggcc acgaaaaaag ggggggcccg   1020
gtac                                                                 1024
```

<210> SEQ ID NO 12
<211> LENGTH: 302
<212> TYPE: PRT
<213> ORGANISM: human

<400> SEQUENCE: 12

```
Met Cys Ala Glu Arg Leu Gly Gln Phe Met Thr Leu Ala Leu Val Leu
1               5                   10                  15
Ala Thr Phe Asp Pro Ala Arg Gly Thr Asp Ala Thr Asn Pro Pro Glu
            20                  25                  30
Gly Pro Gln Asp Arg Ser Ser Gln Gln Lys Gly Arg Leu Ser Leu Gln
        35                  40                  45
Asn Thr Ala Glu Ile Gln His Cys Leu Val Asn Ala Gly Asp Val Gly
    50                  55                  60
Cys Gly Val Phe Glu Cys Phe Glu Asn Asn Ser Cys Glu Ile Arg Gly
65                  70                  75                  80
Leu His Gly Ile Cys Met Thr Phe Leu His Asn Ala Gly Lys Phe Asp
                85                  90                  95
Ala Gln Gly Lys Ser Phe Ile Lys Asp Ala Leu Lys Cys Lys Ala His
            100                 105                 110
Ala Leu Arg His Arg Phe Gly Cys Ile Ser Arg Lys Cys Pro Ala Ile
        115                 120                 125
Arg Glu Met Val Ser Gln Leu Gln Arg Glu Cys Tyr Leu Lys His Asp
    130                 135                 140
Leu Cys Ala Ala Ala Gln Glu Asn Thr Arg Val Ile Val Glu Met Ile
145                 150                 155                 160
His Phe Lys Asp Leu Leu Leu His Glu Pro Tyr Val Asp Leu Val Asn
                165                 170                 175
Leu Leu Leu Thr Cys Gly Glu Glu Val Lys Glu Ala Ile Thr His Ser
            180                 185                 190
Val Gln Val Gln Cys Glu Gln Asn Trp Gly Ser Leu Cys Ser Ile Leu
        195                 200                 205
Ser Phe Cys Thr Ser Ala Ile Gln Lys Pro Pro Thr Ala Pro Pro Glu
    210                 215                 220
Arg Gln Pro Gln Val Asp Arg Thr Lys Leu Ser Arg Ala His His Gly
```

-continued

```
225                 230                 235                 240
Glu Ala Gly His His Leu Pro Glu Pro Ser Ser Arg Glu Thr Gly Arg
                245                 250                 255
Gly Ala Lys Gly Glu Arg Gly Ser Lys Ser His Pro Asn Ala His Ala
            260                 265                 270
Arg Gly Arg Val Gly Gly Leu Gly Ala Gln Gly Pro Ser Gly Ser Ser
        275                 280                 285
Glu Trp Glu Asp Glu Gln Ser Glu Tyr Ser Asp Ile Arg Arg
        290                 295                 300
```